United States Patent
Novini et al.

(10) Patent No.: US 7,876,951 B2
(45) Date of Patent: *Jan. 25, 2011

(54) MACHINE FOR INSPECTING GLASS CONTAINERS

(75) Inventors: Amir R. Novini, Akron, OH (US); Richard A. Sones, Cleveland Heights, OH (US); Richard D. Diehr, Horseheads, NY (US)

(73) Assignees: Emhart Glass S. A., Cham (CH); Applied Vision Corporation, LLC, Cuyahoga Falls, OH (US)

( * ) Notice: Subject to any disclaimer, the term of this patent is extended or adjusted under 35 U.S.C. 154(b) by 988 days.

This patent is subject to a terminal disclaimer.

(21) Appl. No.: 11/585,381

(22) Filed: Oct. 23, 2006

(65) Prior Publication Data

US 2008/0095427 A1 Apr. 24, 2008

(51) Int. Cl.
*G06K 9/00* (2006.01)
(52) U.S. Cl. .................. 382/142; 356/239.4; 356/240.1
(58) Field of Classification Search .................. 382/142
See application file for complete search history.

(56) References Cited

U.S. PATENT DOCUMENTS

| | | | | |
|---|---|---|---|---|
| 3,089,594 A | * | 5/1963 | Early | 209/525 |
| 4,213,042 A | * | 7/1980 | Beach et al. | 250/223 B |
| 4,807,995 A | * | 2/1989 | Dassler et al. | 281/15.1 |
| 5,020,908 A | * | 6/1991 | Hermann | 356/239.1 |
| 5,200,801 A | * | 4/1993 | Juvinall et al. | 356/428 |
| 5,610,391 A | * | 3/1997 | Ringlien | 250/223 B |
| 5,617,204 A | * | 4/1997 | Hinata | 356/239.4 |
| 5,895,911 A | * | 4/1999 | Giometti et al. | 250/223 B |
| 5,900,945 A | * | 5/1999 | Hinata et al. | 356/428 |
| 6,104,482 A | * | 8/2000 | Brower et al. | 356/239.4 |
| 6,275,287 B1 | * | 8/2001 | Watanabe | 356/239.4 |
| 7,414,716 B2 | * | 8/2008 | Sones et al. | 356/239.4 |
| 7,541,572 B2 | * | 6/2009 | Novini et al. | 250/223 B |

* cited by examiner

*Primary Examiner*—Samir A Ahmed
*Assistant Examiner*—Jayesh Patel
(74) *Attorney, Agent, or Firm*—Reinhart Boerner Van Deuren s.c.

(57) ABSTRACT

A machine for inspecting the finish of a glass container rotating at an inspection station. A pair of light sources, which are repeatedly turned on and off, have horizontal light axes which are orthogonally related and intersect the container axis. The light sources illuminate the container finish to identify checks. The illuminated checks are imaged by a camera which has a camera axis coincident with the container axis and the intersecting light axes. The camera axis makes an angle of 45 degrees with both light axes and the horizontal. The camera is exposed through multiple images.

4 Claims, 8 Drawing Sheets

MACHINE FOR INSPECTING GLASS CONTAINERS

The present invention relates to machines, which inspect glass containers for defects, and more particularly, to a system which inspects for cracks in translucent glass containers.

BACKGROUND OF THE INVENTION

In the glass container industry, small cracks or fracture in the glass are referred to as "check defects". Checks can range from sub millimeters to several hundred millimeters and can be oriented at any direction from vertical to horizontal. Glass is not a crystalline structure by nature, but most cracks propagate roughly along a plane of some orientation in space mostly determined by the shape of the glass at that location. For example, a crack that began as a vertical crack at the upper surface of the mouth primarily propagates in a vertical plane. Checks can appear in any orientation and on any portion of a container and can exist wholly within the glass or may penetrate to one or both surfaces. Checks are considered phase objects and do not absorb light like a solid objects does. Checks are primarily reflective in nature if their opposed surface separation is at least half a wavelength of light. However, very few checks with a smaller separation will reflect light and accordingly they will not likely be detectable by direct reflection methods, but they might have scattering points when they penetrate to the one or both surfaces of the container and will scatter light back to the sensors.

Most of these crack defects will drastically weaken the bottle, often causing it to rupture or to leak. Therefore, bottle manufacturers like to remove these containers before they reach filling plants. Checks appearing near the mouth of the containers are called finish checks. In the glass bottle industry, the term "container finish" refers to the portion of the bottle that defines the mouth, threads or beads, and the ring. The upper surface of the mouth is referred as the sealing surface.

Almost all commercially available check detectors work on the principle of reflected light. A conventional check detector consists of a series of continuously operating light spot light sources and associated photodetectors that are positioned so that known checks on a bottle rotating at an inspection station will reflect light from one of the sources to one of the photo-detectors. Signal processing of the photodetector outputs recovers the sharp peaks while rejecting lower frequency signal variations caused by ambient light, reflection from the bottle sidewall, etc.

While commercially available check detectors are successfully deployed on most glass bottle production lines, there are several drawbacks to the approach. A few of those are: many point sensors are required for many possible reflection angles; some sensor angles are difficult to position; additional sensors and lights need to be added as more production defects appear; time consuming setup is required for each type of container; and it is difficult to reproduce the same setup from one inspection line to another.

The following U.S. Pat. Nos. 4,701,612, 4,945,228, 4,958,223, 5,020,908, 5,200,801, 5,895,911, 6,104,482, 6,211,952, and 6,275,287 all relate to devices that detect defects in the finish of a container.

OBJECT OF THE INVENTION

It is an object of the present invention to provide an apparatus for inspecting glass containers, which can detect vertical, horizontal, and any other angle cracks on a bottle which is user friendly and easily adjusted. Another object of this invention is to provide a detector that can detect known types of checks and also any new checks without specific setup requirements.

Other objects and advantages of the present portion of this invention will become apparent from the following accompanying drawings which illustrate, in accordance with the mandate of the patent statutes, a presently preferred embodiment incorporating the principles of the invention.

BRIEF DESCRIPTION OF THE DRAWINGS

The invention will become apparent from the following accompanying drawings which illustrate, in accordance with the mandate of the patent statutes, a presently preferred embodiment.

DETAILED DESCRIPTION OF THE PREFERRED EMBODIMENT

Figure 1:
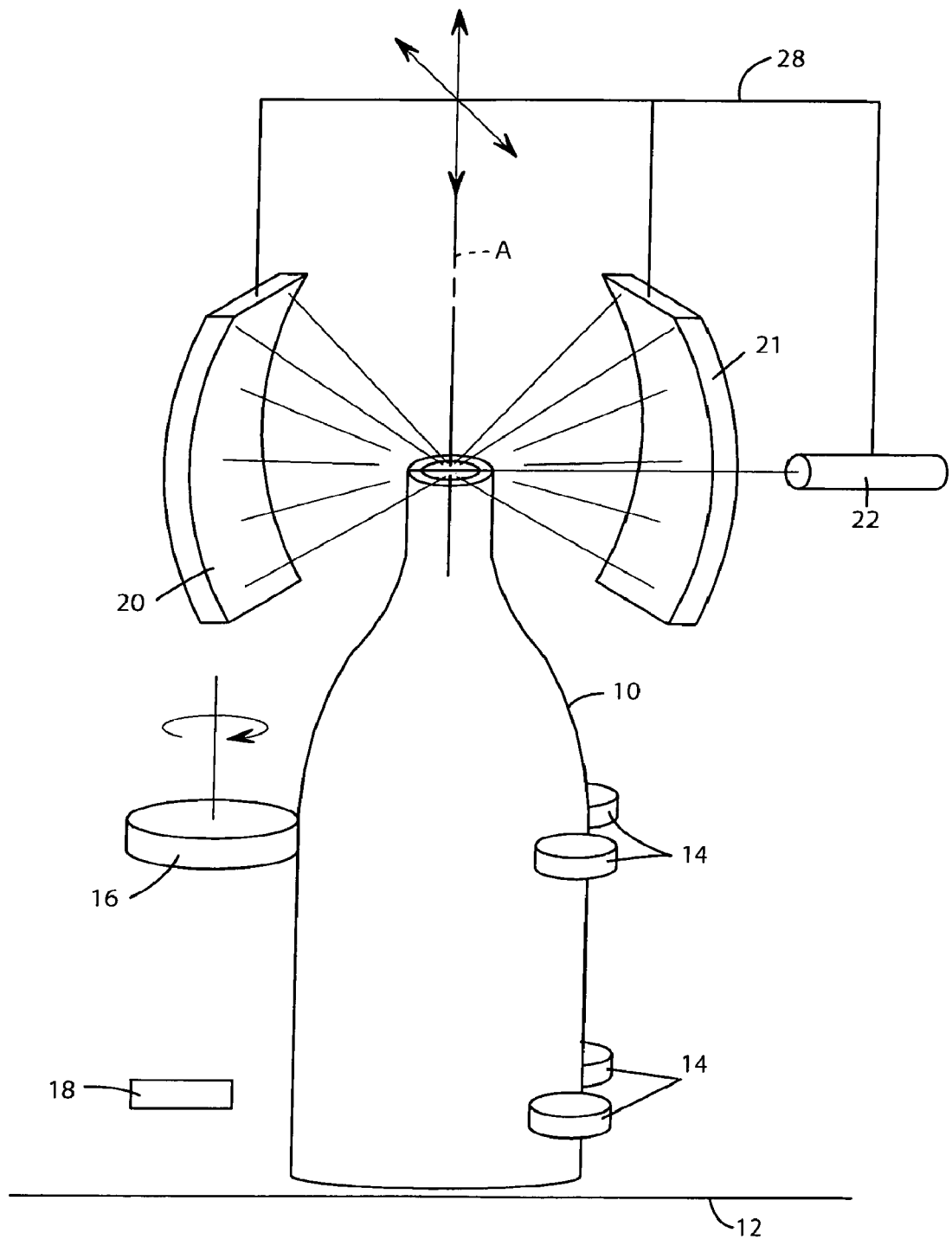
FIG. 1 is an oblique elevational schematic view of an inspection station of a machine for inspecting glass containers for checks and other defects, made in accordance with the teachings of the present invention.

In a machine for inspecting glass containers (bottles), the containers 10 are transported along a conveyor 12 to an inspection station illustrated in FIG. 1. The conveyor may be a linear belt or a turret type feed system. A container 10 is engaged by upper and lower rear pairs of idler rollers 14 and a front drive wheel 16 so that rotation of the drive wheel in the clockwise direction will rotate the container in the counter-clockwise direction. There is conveyor dwell of sufficient duration at the inspection machine so that the container can be rotated more than 360 degrees while the inspection takes place. A container present sensor 18 will sense the presence of a container at the inspection station (the sensor can be upstream and the actual presence of the container at the inspection station could be defined by an encoder count following the sensing of the container by the upstream part present sensor. Light sources (Light Source #1/20 (see FIGS. 1 and 2) and Light Source #2/21) illuminate the finish portion of the container and a Camera/22 images the finish portion.

Figure 2:
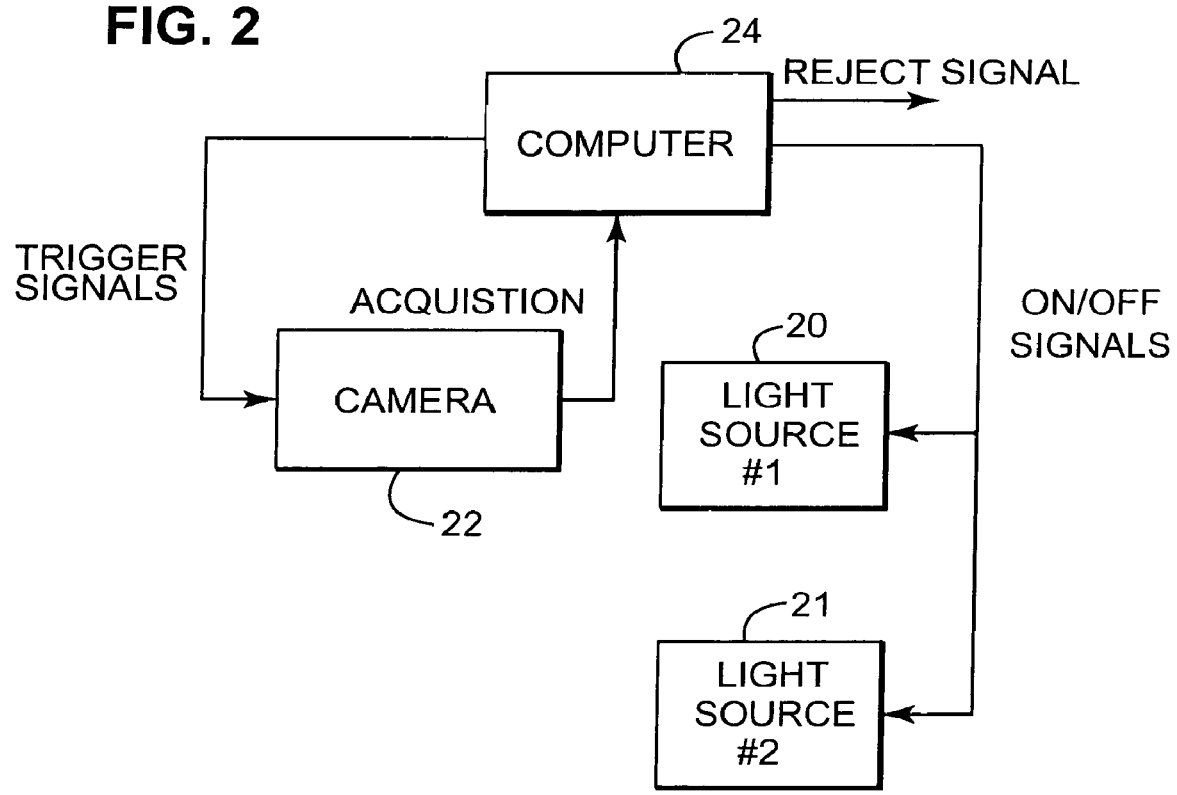
FIG. 2 is a block diagram showing the operation of the pairs of light sources and camera shown in FIG. 1.

FIG. 2 illustrates the operation of the Camera and Light Sources. A Computer 24 delivers On/Off signals to Light Source #1/20 and Light Source #2/21 and delivers Camera Trigger signals to the Camera/22. The Camera has a matrix array of elements (pixels) to receive an image of the finish portion of the container during the Camera's exposure period. The Camera could be a CCD, MOS or like camera which will store an image until the next Trigger Signal. When a Trigger Signal is received, the existing image will be captured and transferred, as an "Acquisition", to the Computer so that it can be recorded and processed by the Computer. The Computer will issue a Reject Signal if a defect is identified.

Figure 3:
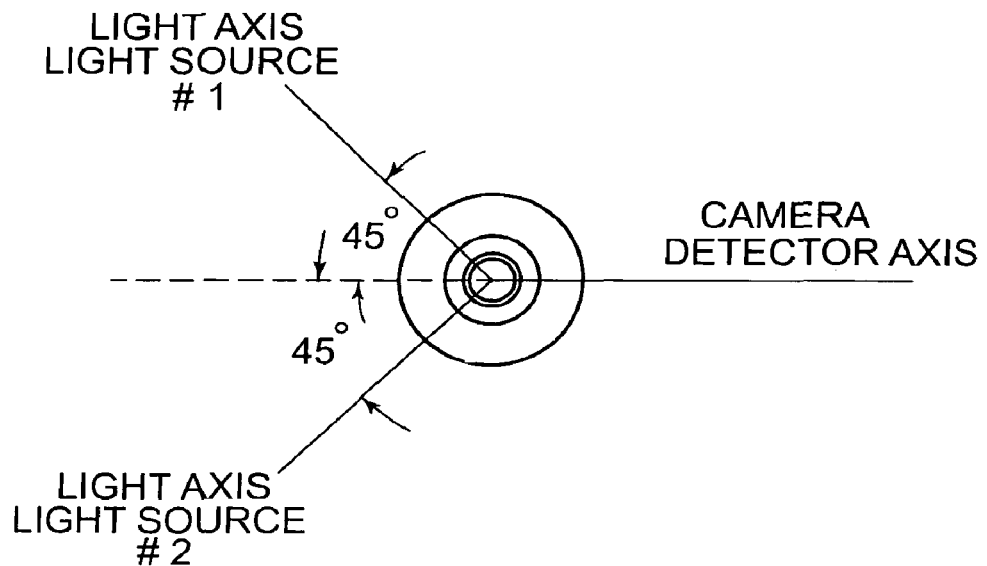
FIG. 3 is a schematic top view of the container at the inspection station showing the light axes of a pair of light sources and the camera.
Figure 4:
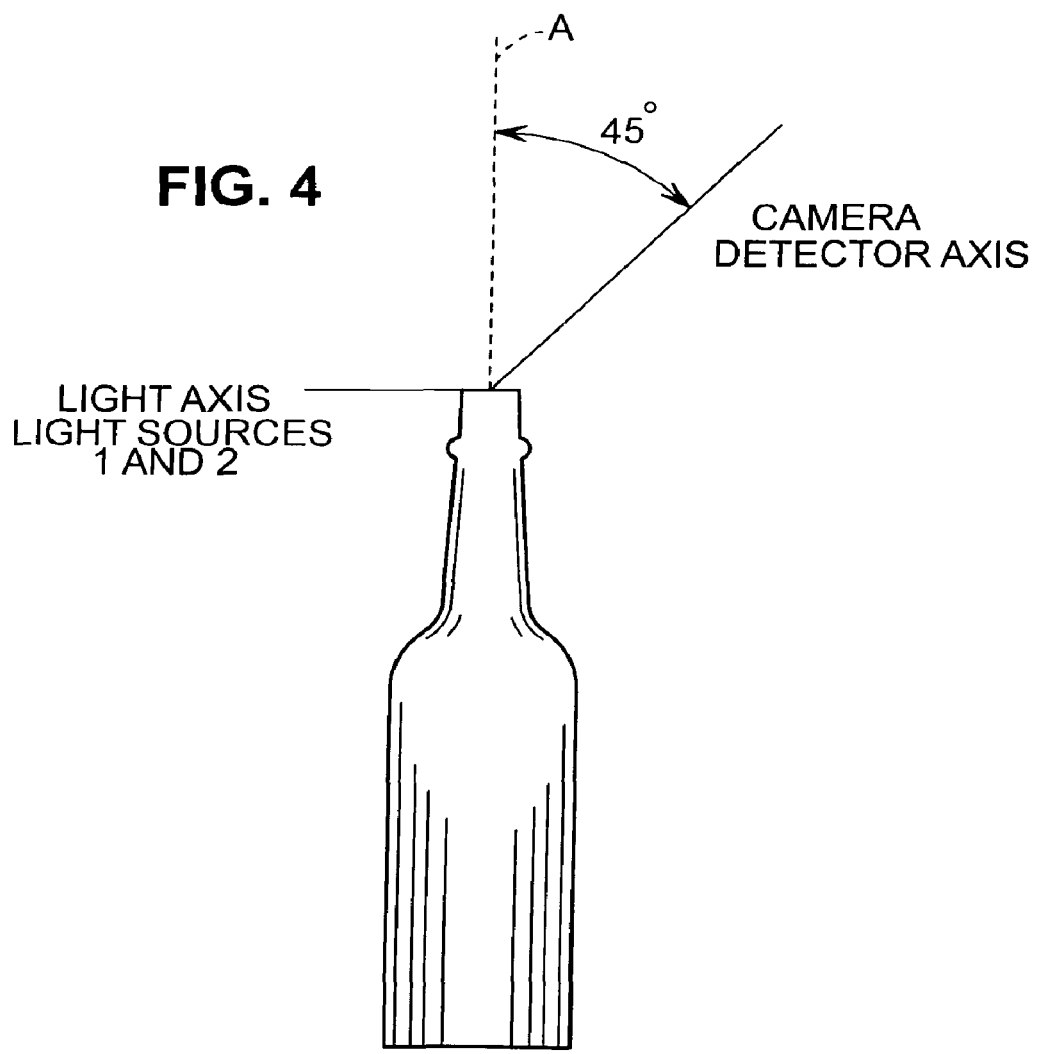
FIG. 4 is a schematic elevational view showing the light axes of the light sources and camera shown in FIG. 3.
Figure 5:
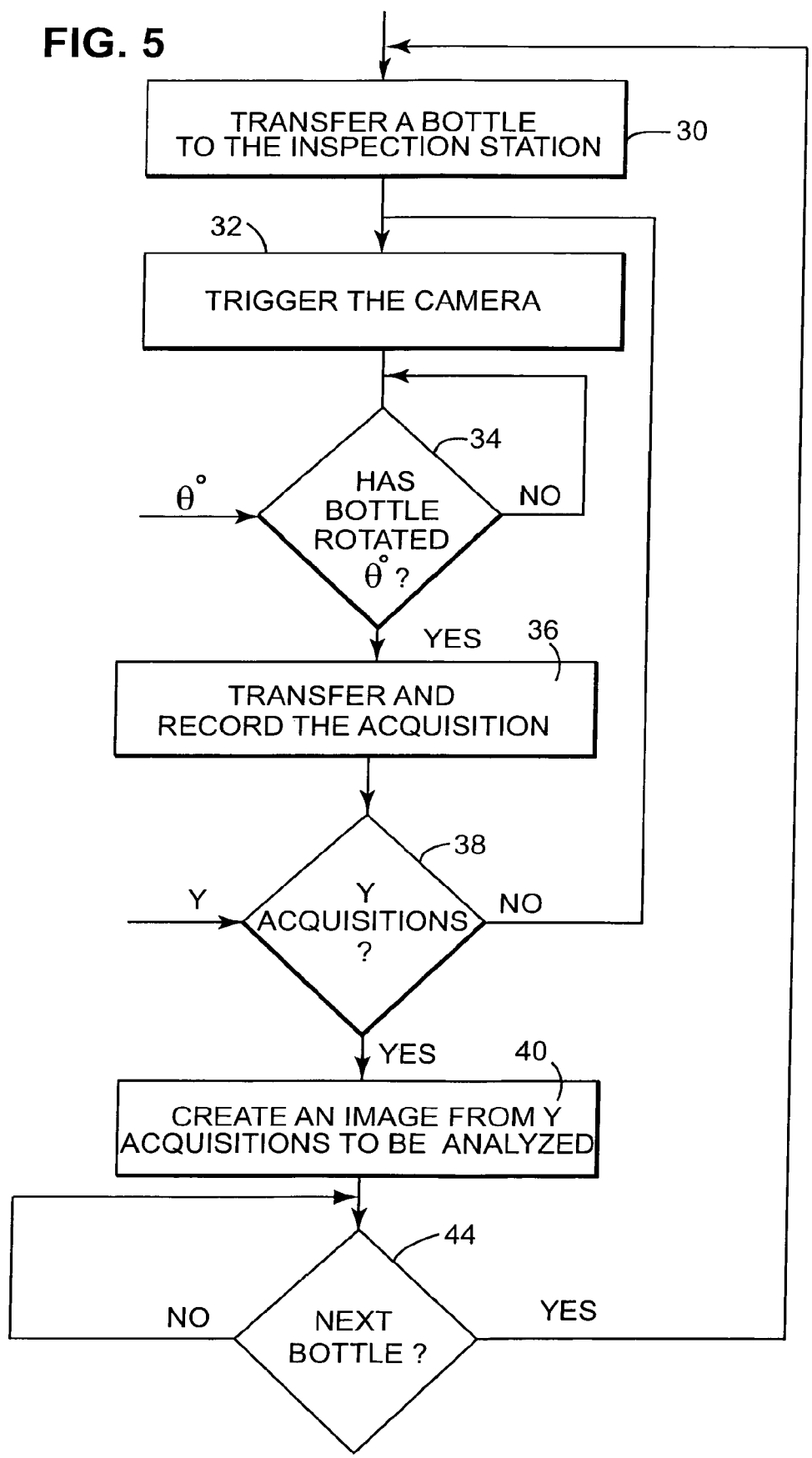
FIG. 5 is a logic diagram illustrating the operation of the camera system of the inspection machine.

As can be seen from FIGS. 3 and 4, the Light Axis for each light source, which is in the positive "Z" plane of the container, is horizontal and intersects the axis "A" of the container. The two light axes are orthogonal to each other and 45° to a vertical plane including the Camera Detector Axis. The Detector Axis for the Camera/22, which is located in the negative "Z" plane, is approximately 45° from horizontal. With this relationship, the camera is looking at a dark field and seeing only light coming from the checks. The light sources and camera are supported by structure 28 that can be vertically displaced and horizontally displaced to reposition the system for different height/diameter containers.

To start an inspection, the machine will Transfer A Bottle To The Inspection Station/30. Following a time sufficient for the rotation of the bottle, by the drive wheel, to become stable, the Computer will Trigger The Camera/32. This starts the acquisition of the image. The following explanation is provided in terms of angles for purposes of clarity, but it should be understood that in a digitally controlled camera, instructions may be time based rather than defining actual angles so that when something is to occur in an approximate θ° (60° angle in the preferred embodiment), an approximate time (number of pulses) may be selected which approximately corresponds to that angle and where events are desired approximately every 7.5°, for example, the pulses could be divided by 8. When the query "Has Bottle Rotated θ°?"/34 (θ° or a selected number of pulses corresponding approximately to that angle of rotation can be set) is answered in the affirmative, the Computer will Transfer And Record The Acquisition/36. Once the Camera is triggered, the Camera will capture data until the Camera is again triggered (following the rotation through θ°). When the Computer answers the query "Y Acquisitions?" in the negative, the Computer will again Trigger The Camera/32. When the computer answers the query "Y Acquisitions?"/38 in the affirmative ("Y' may be set and is six in the preferred embodiment), the Computer will Create An Image From Y Acquisitions To be Analyzed/40. The image created (a Critical Addition), where as in the preferred embodiment "Y" is six, will represent the entire (approximately) 360° surface of the finish and will be the Critical Addition of six acquisitions each imaging eight illuminations.

The critical addition will be made in a manner that will maximize the data that indicates that a defect is present. The Critical Addition can represent for each pixel location, the highest intensity of the corresponding pixel in all six Acquisitions which will make up the Critical Addition. Then, when the Computer answers the inquiry Next Bottle?/44 in the affirmative, the next bottle can be processed.

An image processing technique may be used to enhance the signal created by checks from signal created by mold features of the container. First, a reference or "mask image", can be created using a set of sample containers without defects running through the inspection setup (containers without defects are referred as "good ware" and containers with defects that need to be removed during the inspection as "bad ware"). To incorporate all the signals created by good ware from different molds that may contain slightly different structural variations, and small variations of signals due to vibrations and rotation, a large number of images can be acquired and processed to create the mask image. These images contain almost all the possible variation of light reflection by mold marks, threads, seams, and curved surface of good ware. Mask image is created by combining the all the good ware images. A mask image is created and is compared with the reference mask created with good ware. The difference between the image and the mask shows the signals created by check defects.

Figure 6:
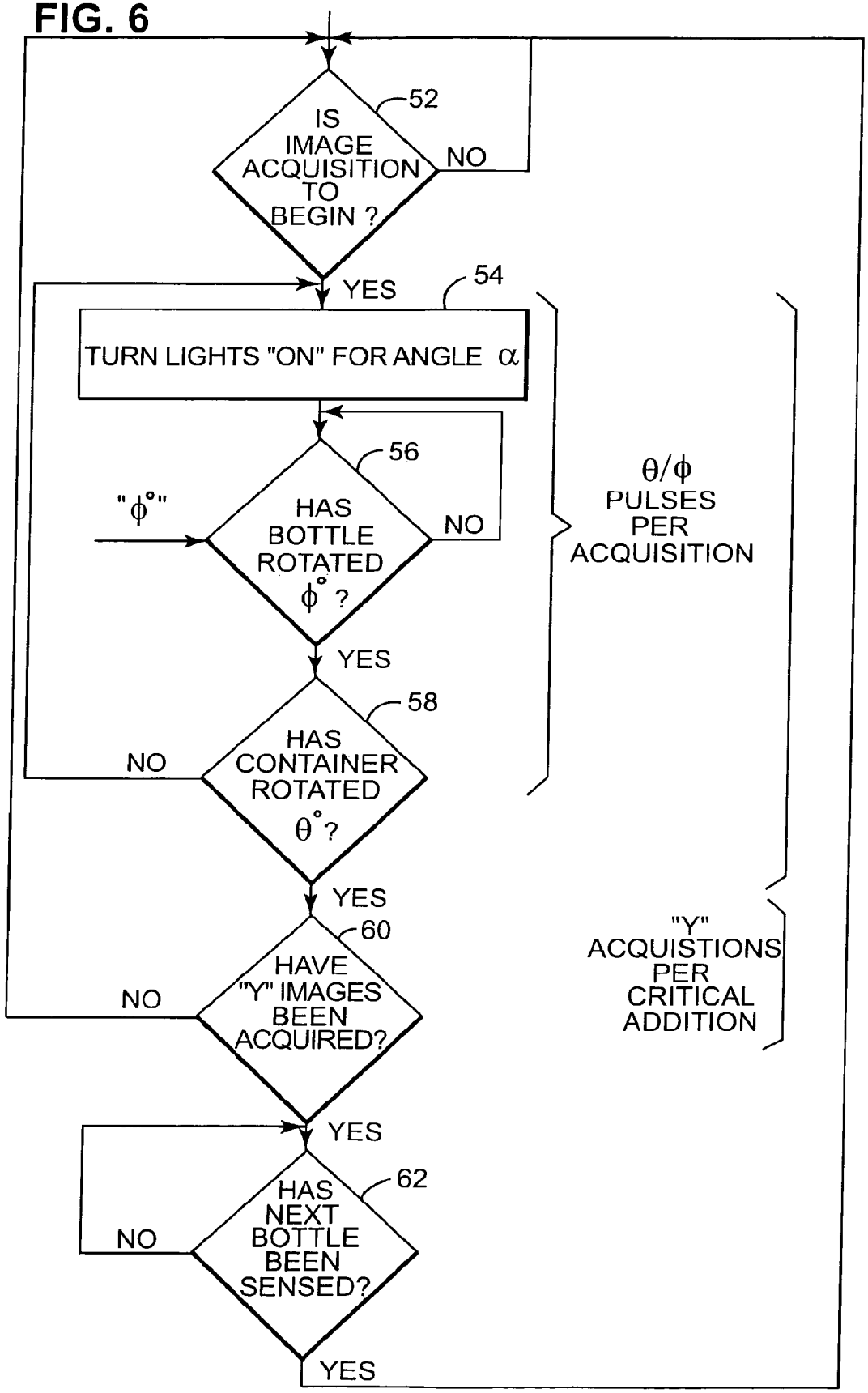
FIG. 6 is a logic diagram illustrating the operation of the lighting system of the inspection machine.

FIG. 6 illustrates the operation of the light sources. When the Computer answers the query "Is Image Acquisition To Begin?"/52 in the affirmative, the Computer will Turn Lights "On" For Angle "α"/54 ("α" may be set and could be a defined number of pulses). When the Computer answers the query "Has Container Rotated "φ°"/56 in the affirmative (φcan be set), and answers the query "Has Container Rotated θ°?"/58 in the negative, the light sources will again be turned "on". When this inquiry is answered in the affirmative (θ/φ pulse per acquisition), and the query Have "Y" Images Been Acquired?/60", in the negative the entire surface has not been imaged and the entire process can be repeated until "Y" images have been acquired (Y pulses per acquisition). Then, when the computer answers the inquiry "Has Next Container Been Sensed?"/62 in the affirmative, the entire process can be repeated for the next bottle. If the lights are to be on for the entire time that the camera is triggered (α can be set to equal θ°).

To reduce noise, α is, in the preferred embodiment, defined so that the surface will be illuminated a small portion (25%) of the angle φ°. Checks that will cause a container to be rejected have been found to be imaged when the light sources are "on" only a small fraction of α. This fraction can be empirically varied to achieve a desired result. While the imaging process has been disclosed with reference to checks in the finish area of the container, it can be used to identify body or heel checks and other defects.

Figure 7:
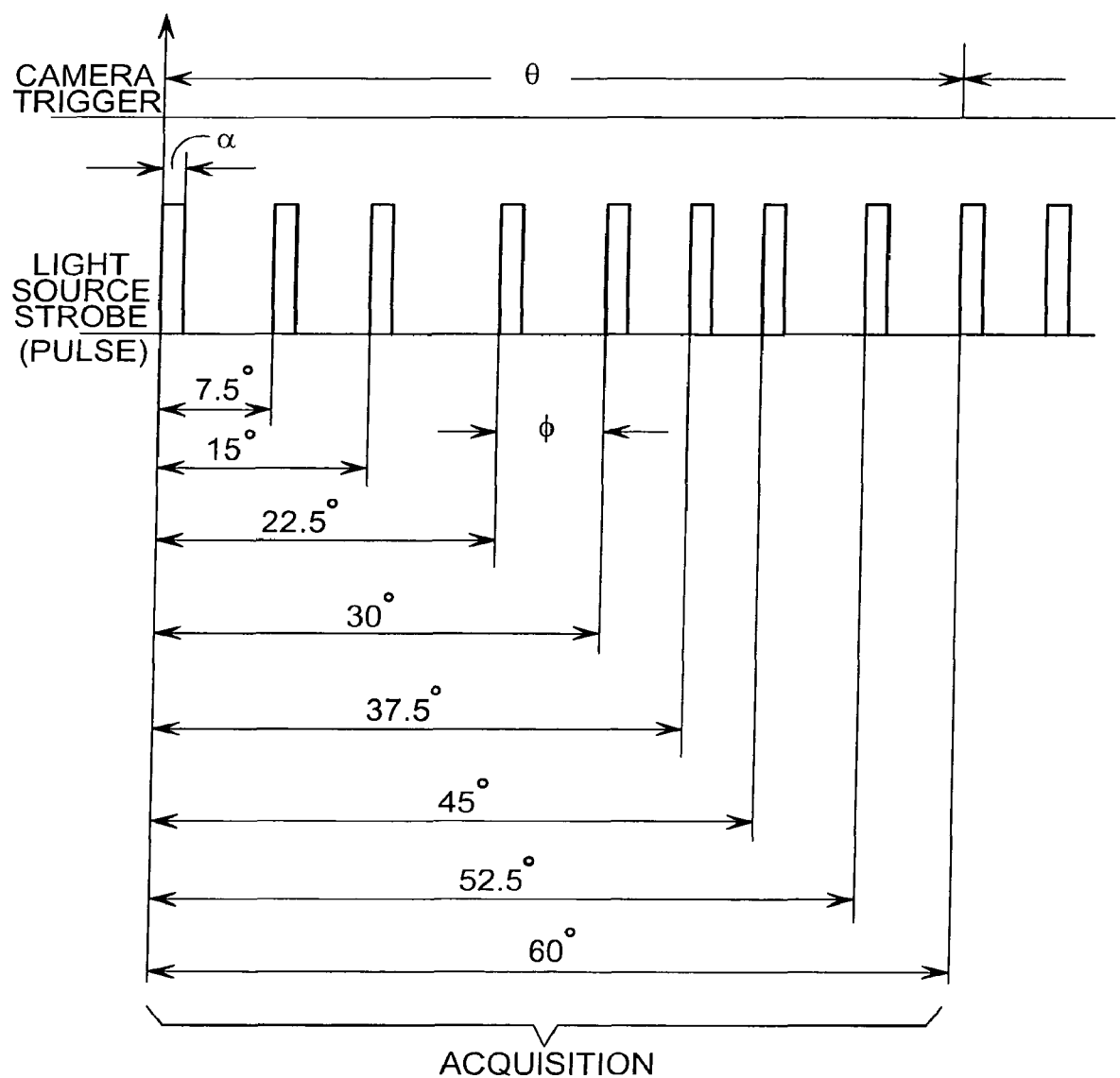
FIG. 7 is a timing diagram illustrating the operation of the light sources.

FIG. 7 is a timing diagram for an Acquisition comprised of light sources turned on α degrees for every φ° (7.5° in the preferred embodiment) through θ° (60° in the preferred embodiment). The lower the ratio of α/φ°, the less noise will be available to interfere with the desired signal.

Figure 8:
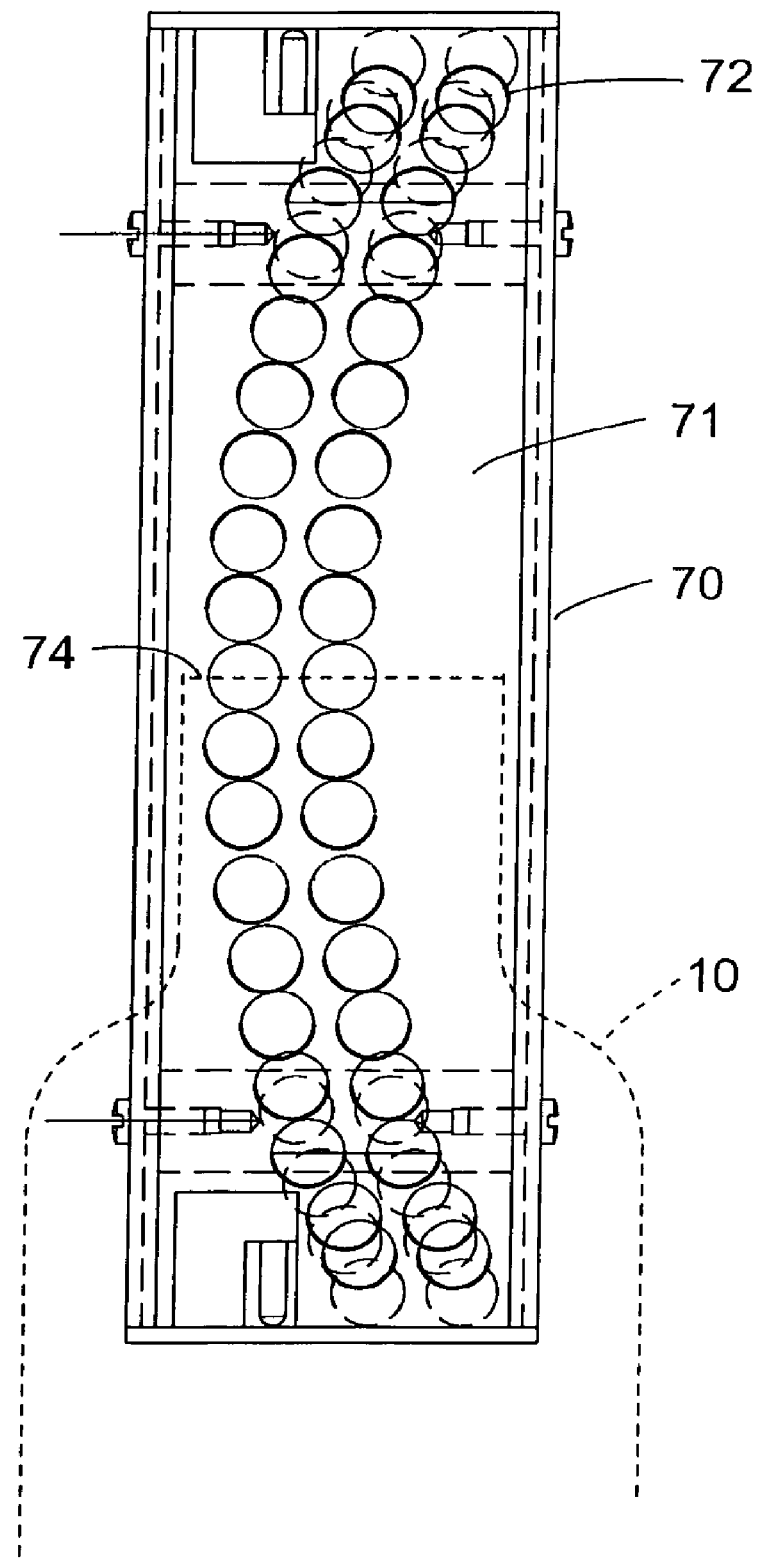
FIG. 8 is a side elevational view of one of the light sources.
Figure 9:
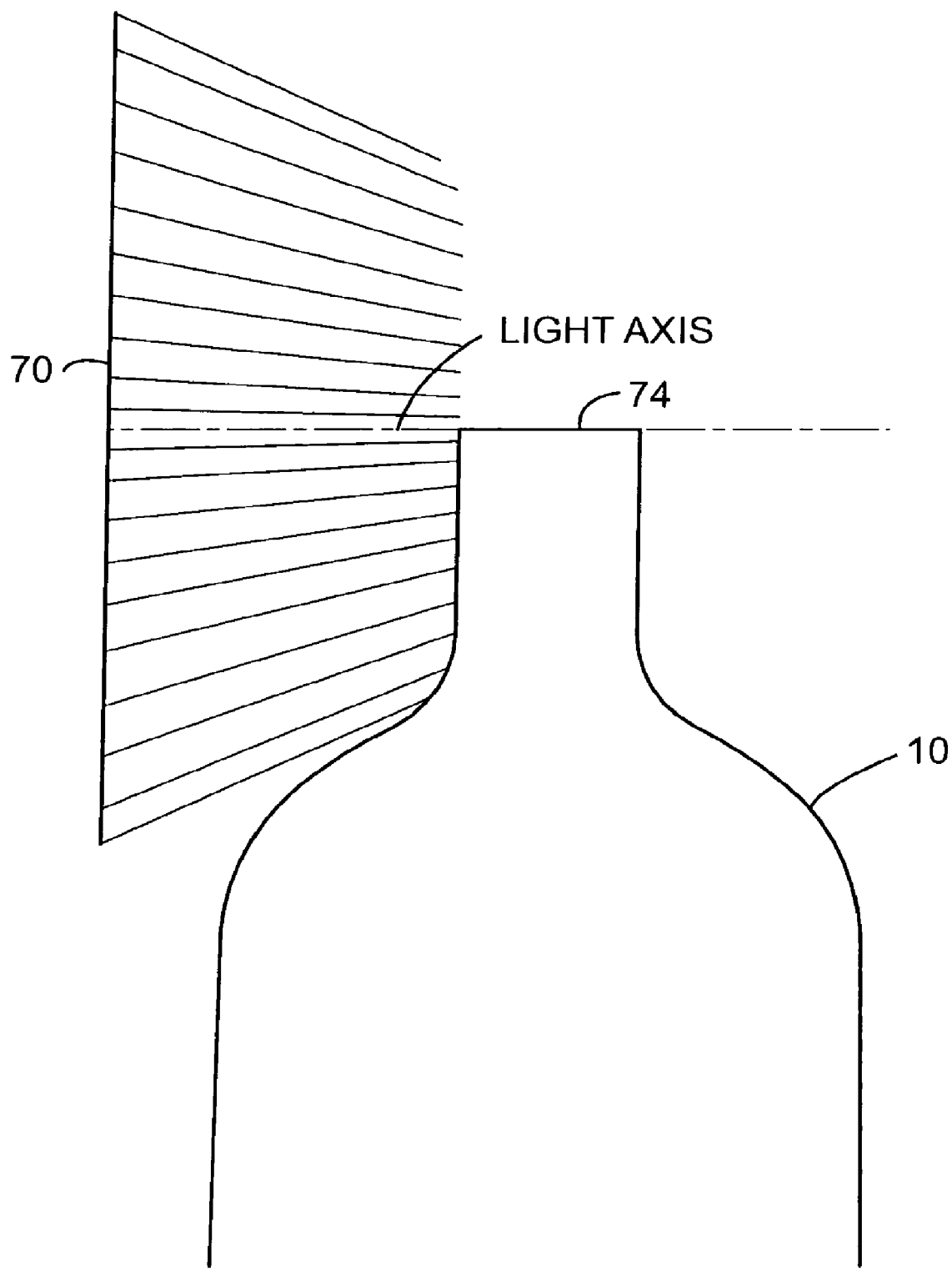
FIG. 9 is an elevational view showing how the LED's of one of the light sources are aimed toward the finish.

The light sources 70 (FIGS. 8 and 9) are mirror images and are segments of an arc. As shown the light source, mounted on a flat panel 71, is perpendicular to the Light Axis and faces the finish of the container 10 which is shown in dotted lines. The segment has inner and outer (or three or four, . . . ) rows of LED's 72 with the central LED's 74, which define the Light Axis, standing parallel to the Light Axis and with the remaining LED's being progressively tilted toward the light axis as they proceed away from the Light Axis. The preferred location of the Light Axis is at the sealing surface 74 but it can be located from the sealing surface to the bottom of the finish. The ideal geometry that the preferred embodiment attempts to approach is that of conical illumination, where the top and bottom of the cone are dark so that the camera will not see any direct reflections of light. Viewing the finish as a torus, this conical geometry allows the maximum light to be projected onto the finish with direct reflection. Only an anomaly in the finish (a check) will generate direct reflections to the camera.

This apparatus has following advantages: because the area sensor image an area of the bottle, it is possible to detect almost all the checks in that region. This means the inspection is independent of the specific orientation and location of the check, and thus enables detecting "new" checks without changing the setup. The positioning of the area array sensors and light sources would not depend essentially on the geometry of the bottle. It will be easier to setup for most of the containers with little or no adjustments.

The invention claimed is:

1. A machine for inspecting the finish area of a vertical glass container at an inspection station comprising means for rotating the glass container at the inspection station, first and second vertically extending light sources each having a light axis for illuminating a selected portion of the rotating glass container, the light axis of each of said first and second light sources being horizontal, substantially in the same horizontal plane as the finish of the glass container, intersecting proximate the axis of the glass container at the finish, and defining between them an orthogonal angle, said light sources having a selected "on" time followed by a selected "off" time, means for turning said light sources "on" and "off" a plurality of consecutive times, a camera having a detector axis intersecting said glass container axis with said light axes and defining an angle of approximately 45 degrees above the horizontal and 45 degrees with each light axis, said camera including a triggerable imaging portion for imaging the selected illuminated portion of the glass container, said camera having an exposure time at least equal to the time required for the rotating glass container, said camera having an exposure time at least equal to the time required for the rotating glass container to rotate through said defined angle of rotation, means for triggering the imaging portion of said camera when the bottle is at the beginning and end of said defined angle of rotation so that the camera will image said selected portion of the container as said glass container rotates through said defined angle of rotation, and means for capturing and transferring the image when the trigerring means is triggered at the end of said defined angle of rotation.

2. The machine for inspecting the finish area of a glass container at an inspection station according to claim 1, wherein said first light source is a vertical array of LED's including at least one LED defining the first light source light axis and wherein said second light source is a vertical array of LED's including at least one LED defining the second light source light axis.

3. The machine for inspecting the finish area of a glass container at an inspection station according to claim 2, wherein each light source includes a first plurality of LED's extending vertically below the LED defining the light axis for that light source.

4. The machine for inspecting the finish area of a glass container at an inspection station according to claim 3, wherein each of said first plurality of LED's is progressively tilted toward the first light source light axis as a function of distance from the first light axis and wherein each of said second plurality of LED's is progressively tilted toward the second light source light axis as a function of the distance from the second light axis.

\* \* \* \* \*